United States Patent [19]

Markwell et al.

[11] Patent Number: 5,432,064
[45] Date of Patent: Jul. 11, 1995

[54] **PROCESS FOR DEPHOSPHORYLATING LINEAR POLYNUCLEOTIDE SUBSTRATE WITH PROSPHATASE FORM *ASPERGILLUS NIGER***

[75] Inventors: John P. Markwell, Lincoln, Nebr.; Wayne K. Versaw, Madison, Wis.; John C. Osterman, Waverly; Philip M. Kelley, Lincoln, both of Nebr.

[73] Assignee: Board of Regents of the University of Nebraska, Lincoln, Nebr.

[21] Appl. No.: 959,543

[22] Filed: Oct. 13, 1992

Related U.S. Application Data

[62] Division of Ser. No. 605,539, Oct. 29, 1990, Pat. No. 5,183,752.

[51] Int. Cl.[6] .................. C12N 9/16; C12N 1/14; C12N 1/00; C12P 19/34
[52] U.S. Cl. .................. 435/91.1; 435/196; 435/254.3; 435/917
[58] Field of Search .................. 435/91, 196, 171, 917

[56] References Cited

PUBLICATIONS

Jarayaman et al., Madras. Agr. J., V59, N11–12, pp. 640–641, 1972.
Ternynck et al., Ann. Immunol. (Inst. Pasteur), vol. 127 C, pp. 197–208, 1976.
Rokosu et al., Int. J. Biochem., vol. 11, pp. 541–4, 1980.
Rokosu et al., Experientia, vol. 38, pp. 78–79, 1982.
Ramaswamy et al., Experientia, vol. 32, No. 7, pp. 852–853, 1976.
Trembacz et al., J. Biochem., vol. 271, pp. 621–625, 1990.
Le'John et al., BBRC, vol. 66, No. 2, pp. 460–467, 1975.

*Primary Examiner*—David M. Naff
*Assistant Examiner*—Michael V. Meller
*Attorney, Agent, or Firm*—John P. Floyd

[57] ABSTRACT

The present invention relates to the preparation of a novel heat-labile phosphatase enzyme from the filamentous fungus *Aspergillus niger*. This *A. niger* phosphatase enzyme has a native molecular weight of approximately 80,000 daltons, and is shown by polyacrylamide gel electrophoresis under denaturing conditions to be an alpha-2 dimer consisting of identical subunits of molecular weight of approximately 37,000 daltons each. The native intact enzyme molecule has an isoelectric point (pI) of 4.6, and exhibits optimal functional activity under reaction conditions of neutral to slightly alkaline pH conditions (about pH 7.0 to about pH 8.5). This enzyme has two characteristics which make it valuable in molecular biology laboratory protocols. First, the enzyme is readily inactivated by mild heating conditions (50° C.); and second, the enzyme is highly specific for DNA as a substrate for the hydrolysis reaction; it does not hydrolyze adenosine triphosphate (ATP). This unique characteristic permits the simultaneous dephosphorylation and labeled rephosphorylation of DNA in the presence of polynucleotide kinase and labeled ATP, and eliminates the requirement for a multiplicity of steps in this DNA end-labeling process.

5 Claims, 1 Drawing Sheet

PROCESS FOR DEPHOSPHORYLATING LINEAR POLYNUCLEOTIDE SUBSTRATE WITH PROSPHATASE FORM *ASPERGILLUS NIGER*

This application is a division of application Ser. No. 07/605,539, filed Oct. 29, 1990, now U.S. Pat. No. 5,183,752.

BACKGROUND OF THE INVENTION

The present invention relates to a new phosphatase enzyme. In particular, the present invention relates to the discovery of a novel heat-labile phosphatase enzyme from the filamentous fungus *Aspergillus niger*. This new phosphatase enzyme is used as a highly-specific reagent for the hydrolytic removal of terminal phosphate groups from linear DNA molecules during one-step radioactive end-labeling procedures, as well as during preparation of linear DNA molecules for use in molecular cloning assays.

In the following discussion, a number of citations from professional journals are included for the convenience of the reader. While these citations will more fully describe the state of the art to which the present invention pertains, the inclusion of these citations is not intended to be an admission that any of the cited publications represent prior art with respect to the present invention.

To place this new microbe-derived phosphatase enzyme in perspective, it will be helpful to provide some background for the molecular processes in which phosphate groups are transferred among cytoplasmic constituents in a normal cell. In the action of many polypeptide hormones, a critically-important cellular mediator is the "second messenger" protein called cyclic adenosine monophosphate (cAMP), which is formed from adenosine triphosphate (ATP) by the enzyme adenylate cyclase; this latter enzyme is bound to the cytoplasmic side of plasma membranes (see Watson et al., *Molecular Biology of the Gene* (4th Edition), The Benjamin/Cummings Publishing Company, Menlo Park, Calif., 1987). After its synthesis, cAMP works by stimulating the activity of cAMP-dependent enzymes called protein kinases. Protein kinases are enzymes that transfer the high-energy terminal phosphate group of ATP to specific amino acids (serine, threonine, or tyrosine residues) on target proteins. Phosphorylation (i.e., the process of adding a phosphate group to a protein) alters the enzymatic activities of these target proteins, and, depending on the particular enzymes involved and the location of the added phosphate moiety, can either raise or lower their functional activities.

In a like manner, removal of a phosphate group from a protein (a process known as "dephosphorylation") can also greatly modify the functions and activities of certain biological molecules. Dephosphorylation occurs by a process of "hydrolysis" in which the phosphate group is catalytically broken away ("lysed") from a parent molecule by the enzymatic addition of a water molecule to the parent molecule. This ongoing and cyclic process of phosphorylation followed by dephosphorylation, as well as dephosphorylation followed by rephosphorylation, are essential processes in the energy-efficient functioning of all living cells.

The dephosphorylation of a linear DNA molecule by the removal of the highly-reactive terminal 5'-phosphate group is an essential step in a number of molecular cloning protocols. Removal of the highly-reactive terminal phosphate prevents the linear DNA molecule from spontaneously ligating to the 3'-hydroxyl group at the opposite end of the same molecule, or to terminal hydroxyl groups on other reactive "bystander" DNA molecules in the same reaction mixture. In addition to this important "house-keeping" function, the dephosphorylation reaction is used by research investigators to prepare the reactive 5'-ends of a linear DNA molecule for subsequent radioactive end-labeling in the presence of polynucleotide kinase and [gamma-$^{32}$P]-ATp, as will be discussed more fully hereinafter.

Currently, the enzyme most widely used in molecular biology protocols for the removal of the terminal 5'-end phosphates from DNA molecules is calf intestine alkaline phosphatase (as discussed in the recent volume by Maniatis T., Fritsch E. F., and Sambrook J. (editors): *Molecular Cloning: A Laboratory Manual*; New York: Cold Spring Harbor Laboratory, pages 133–134, 1982). When used in any of a variety of molecular cloning procedures, this bovine-derived enzyme has the advantage over other previously-used phosphatases in that it can be completely denatured (with total loss of activity) by heating the reaction mixture to 68° C. in the presence of an additional denaturing agent such as the negatively-charged detergent sodium dodecyl sulfate (SDS). Under these conditions, the calf intestine alkaline phosphatase is completely destroyed without denaturing the DNA in the reaction mixture. This is important because the native calf enzyme has the capacity to react with a wide variety of phosphate-bearing substrates, including the energy-rich molecule adenosine triphosphate (ATP). Because of this capacity to react with ATP, it is absolutely necessary to inactivate or remove the calf phosphatase after the dephosphorylation reaction is complete, in order to prevent its interfering with phosphate transfer from ATP in the subsequent reaction steps of an end-labeling protocol.

The fairly low inactivation temperature of 68° C. is an important factor in the current selection of calf intestine alkaline phosphatase for use in molecular cloning and end-labeling protocols. Other alkaline phosphatases, derived from such sources as the bacterium *Escherichia coli*, can only be inactivated by boiling the reaction mixture in which that enzyme is contained. Such harsh temperatures (at least 100° C.) are likely to denature more than just the phosphatase enzyme, and may cause irreversible damage to the DNA as well. Furthermore, it is not clear that boiling is sufficient to completely inactivate the *E. coli* phosphatase, making the use of this microbial enzyme even less attractive.

While working with the calf intestine alkaline phosphatase does present some significant advantages over using other phosphatase enzymes, there are disadvantages. For example, the need for the combination of heating the reaction mixture to 68° C. and using SDS to inactivate the calf enzyme is cumbersome. In radioactive end-labeling procedures, for example, use of these procedures necessitates a multiplicity of reaction steps in order to eliminate the enzyme. The DNA must be precipitated from the reaction mixture, washed, and then re-isolated free of the enzyme before the DNA is used as target substrate for reactivity with other phosphate-bearing molecules in subsequent reaction steps. These multiple steps of heating, precipitating, washing and re-isolating DNA molecules are a real disadvantage in studies in which such factors as time, or temperature (or both) are critical.

Additional disadvantages which are evident when working with the calf-derived enzyme, as well as with the *E. coli*-derived phosphatase, are their broad reaction specificities (i.e., both have the capacity to dephosphorylate more than just DNA molecules). Furthermore, it is clear that enzymes derived from mammalian sources are not as convenient to obtain as they are from microbial sources; accordingly, mammalian-derived enzymes have associated with them certain economic disadvantages, which, depending on the enzyme source, can be very significant. Consequently, there is a need for finding an alternate source (preferably microbial) for phosphatase enzymes. This has been the objective of much research.

An important microbial source which has been well studied over the years is the filamentous fungus *Aspergillus niger* (hereinafter "*A. niger*"). Several phosphatase enzymes have been isolated from this microbial organism, and have been found to exhibit a broad substrate specificity (not unlike that of calf intestine alkaline phosphatase). With regard to functional characteristics, they have been generally categorized as being either "acid" or "alkaline" phosphatases, i.e., categorized according to the pH value at which their enzymatic function is optimal in the hydrolysis reaction associated with the dephosphorylation process: pH 2.5 to 5 and pH 8.5 to 9.5, respectively. Two reports have suggested the presence of as many as five acid phosphatase activities (i.e., pH 2.5 to 5.0) in extracts of *A. niger* (Komano T, Plant Cell Physiol. 16: 643–658, 1975; Pathak and Sreenivasan, Arch. Biochem. Biophys. 59: 366–372, 1955); two other reports have indicated the presence of several alkaline phosphatase activities from *A. niger* (functional pH optima from pH 8.5 to 10) (Rokosu and Uadia, Int. J. Biochem. 11: 541–544, 1980; Ramaswamy and Bheemeswar, Experientia 32: 852–853, 1976). These alkaline phosphatases, like the calf intestine alkaline phosphatase, have also been reported to exhibit a broad hydrolytic reactivity on substrates which include sugar phosphates, nucleotides such as adenosine-5'-phosphate, small synthetic substrates such as 4-nitrophenylphosphate, and inorganic pyrophosphate ($P \sim P$).

Phosphatase enzymes with a much more limited substrate specificity have also been found in microorganisms. Examples of such restrictive enzyme activity are the phosphomonoester hydrolases. One such enzyme is 4-nitrophenylphosphatase, which is highly specific for synthetic 4-nitrophenylphosphate (4-NPP) as a substrate. While this small substrate molecule is chromogenic before it is hydrolysed by the phosphatase enzyme, its chromophore is revealed only after hydrolysis, and this is shown by a significant increase in the absorption of blue light by the hydrolysed substrate.

Several distinct forms of this 4-nitrophenylphosphatase enzyme have been isolated from cells of the yeast *Saccharomyces cerevisiae* (Attias and Bonnet, Biochim. Biophys. Acta 268: 422–430, 1972), and have been found to function best in an environment having a pH optima between pH 8.0 and 8.5. Further characterization of these yeast-derived enzymes has shown that their functional activities are modified by the presence of certain divalent cations; such information is very important when preparing culture media in which to grow the microorganisms and to perform the test reactions. For example, these yeast-derived phosphatases are strongly activated by magnesium ($Mg^{2+}$) ions, and are inhibited by zinc ($Zn^{2+}$) ions.

The novel phosphatase enzyme of the present invention was discovered in cultures of *A. niger*. A 4-nitrophenylphosphatase activity was unexpectedly found in extracts of homogenized filamentous structures known as "mycelia." The 4-nitrophenylphosphatase extracted from these *A. niger* mycelia exhibited optimal enzymatic activity in a neutral-to-slightly alkaline pH environment (i.e., about pH 7.0 to about pH 8.5). Similar to the *S. cerevisiae* enzyme noted above, the *A. niger* phosphatase activity is markedly stimulated by magnesium ions, and is inhibited by cations of zinc. While being highly specific for 4-NPP as a synthetic substrate, the neutral *A. niger* phosphatase has physical and functional characteristics which distinguish it from the other phosphatase enzymes from calf, *E. coli*, and *A. niger*. For example, the new *A. niger* enzyme exhibits a unique and remarkable substrate specificity; it will interact with the 5'-terminal phosphate of a linear and polymeric DNA molecule, but it unexpectedly will not interact with the terminal phosphate group of a monomeric ATP molecule which may simultaneously be present as a phosphate donor in the same reaction mixture. This subtrate specificity is both remarkable and unexpected.

In stark contrast to the other phosphatases mentioned above, this new *A. niger* phosphatase is very heat labile, being completely inactivated by heating to about 50° C. No denaturing agents, such as the detergent SDS, are needed to facilitate inactivation of this enzyme, as is necessary with the calf-derived alkaline phosphatase. It is very simple, therefore, to destroy the functional activity of this *A. niger* phosphatase (as is especially necessary when the dephosphorylated DNA substrate is to be subsequently used in a molecular cloning procedure) without risking damage or change to any of the other molecules contained in the reaction mixture.

Furthermore, this *A. niger* phosphatase functions best in a reaction environment which is neutral to slightly alkaline (i.e., between about pH 7.0 to 8.5). This is in significant contrast to the other microbial phosphatases tested which require either strongly acid (pH 2.5 to 5.5) or strongly basic conditions (pH 8.5 to 10) for optimal functional activity.

The novelty of this new *A. niger* phosphatase enzyme will become apparent in the following discussion.

SUMMARY OF THE INVENTION

In accordance with the present invention, a purified heat-labile phosphatase enzyme from the filamentous fungus *Aspergillus niger* is provided. This enzyme has a native molecular weight of approximately 80,000 daltons, and, under denaturing conditions, consists of two identical polypeptide subunits, i.e., an alpha-2 dimer, each subunit having a molecular weight of approximately 37,000 daltons. In determining the native molecular charge of this protein, it is found in electrofocusing studies to have an isoelectric point (a "pI") of approximately 4.6. Its enzymatic activity is optimal under neutral to slightly alkaline culture conditions of between about pH 7.0 to about 8.5. Production of *A. niger* phosphatase activity is not repressed by growth on media containing inorganic phosphorus nor is it stimulated by growth on media containing very limited amounts of inorganic phosphorus. The functional activity of this enzyme is stimulated in the presence of magnesium cations ($Mg^{2+}$), and to a lesser extent by manganese ions ($Mn^{2+}$), but it is significantly inhibited by zinc ($Zn^{2+}$) and by calcium ($Ca^{2+}$).

This novel phosphatase enzyme, isolated by procedures described in detail hereinafter, is useful in hydrolysis reactions in which terminal 5'-phosphates are removed from DNA molecules. This hydrolytic removal of 5'-terminal phosphate groups from DNA is an enzymatic process called "dephosphorylation." Exemplary of the use of such a dephosphorylation process is the removal of 5'-terminal phosphate groups from DNA during radioactive end-labeling procedures. Another example is the dephosphorylation of linear DNA molecules in molecular cloning assays to prevent self-ligation, i.e., to prevent the spontaneous or enzyme-catalyzed ligation of the highly-reactive 5'-terminal phosphate on one end of a linear DNA molecule to the 3'-hydroxyl reactive moiety on the opposite end of the same molecule (or, alternatively, to the 3'-hydroxyl ends of other "bystander" DNA molecules in the mixture.) Yet another example is the dephosphorylation of RNA molecules for end-labeling in molecular biological studies.

Like other phosphatase enzymes, the functional hydrolytic activity of this *A. niger* enzyme has usually been measured against the non-biological (synthetic) substrate 4-nitrophenylphosphate (4-NPP), which absorbs blue light when it is hydrolysed. This chemical transformation of 4-NPP is easily detected, and is quantifiable in a standard spectrophotometer. Thus, the *A. niger* phosphatase of the present invention exhibits high specificity for 4-NPP, and, correspondingly, for the terminal 5'-phosphate on DNA, which is a polymeric nucleotide molecule. However, the *A. niger* phosphatase exhibits, remarkably, virtually no reactivity with other substrates, including the monomeric nucleotide ATP. A variety of sugar phosphates, nucleotides, organic phosphates and inorganic pyrophosphates are not hydrolyzed by the *A. niger* enzyme. Neither does this enzyme possess protein phosphatase activity.

The removal of 5'-terminal phosphate groups is effected during procedures designed to replace the 5'-terminal phosphate group with a labeled phosphate group. In a preferred embodiment, these procedures involve a rapid dephosphorylation and rephosphorylation step, at an effective temperature and pH, in the presence of a polynucleotide kinase and an adenosine triphosphate (ATP) molecule bearing a labeled phosphate group. The labeled phosphate group of some large molecules have been labeled with a member selected from the group consisting of a radioactive isotope, an enzyme, a chromophore and a fluorochrome, and detection of this labeled phosphate group has been by means appropriately selected from the group consisting of a radiometric means, an enzymatic means, a chromophorometric means and a fluorometric means. However, in a preferred embodiment of the present invention, the labeled phosphate group on ATP is labeled with radioactive phosphorus-32 (i.e., $^{32}P$). This label, and procedures for its use, is discussed in the recent volume by Maniatis T., Fritsch E. F., and Sambrook J.: *Molecular Cloning: A Laboratory Manual.* New York: Cold Spring Harbor Laboratory, 1982.

Thus, this new enzyme is distinguished from other phosphatases because it is: (1) reactive with DNA, but not with ATP; and (2) heat labile at 50° C., even in the absence of denaturing agents such as SDS. At 50° C., it has a half-life of only 5.3 minutes. These characteristics provide this new phosphatase enzyme with great versatility, compared with other available phosphatase enzymes, for the following reasons:

a. because it does not interact with ATP, this *A. niger* phosphatase can be used in molecular end-labeling and/or molecular cloning procedures in which phosphate-bearing substrates in addition to DNA are present in the same reaction mixture; and b. should it be necessary, the activity of the enzyme of the present invention can be simply and completely abrogated by heating the reaction mixture which contains this enzyme to only 50° C.; no special inhibiting ligands or denaturing reagents are required to bind and/or inactivate the enzyme.

DETAILED DESCRIPTION OF THE INVENTION

EXAMPLE 1

Figure 1:
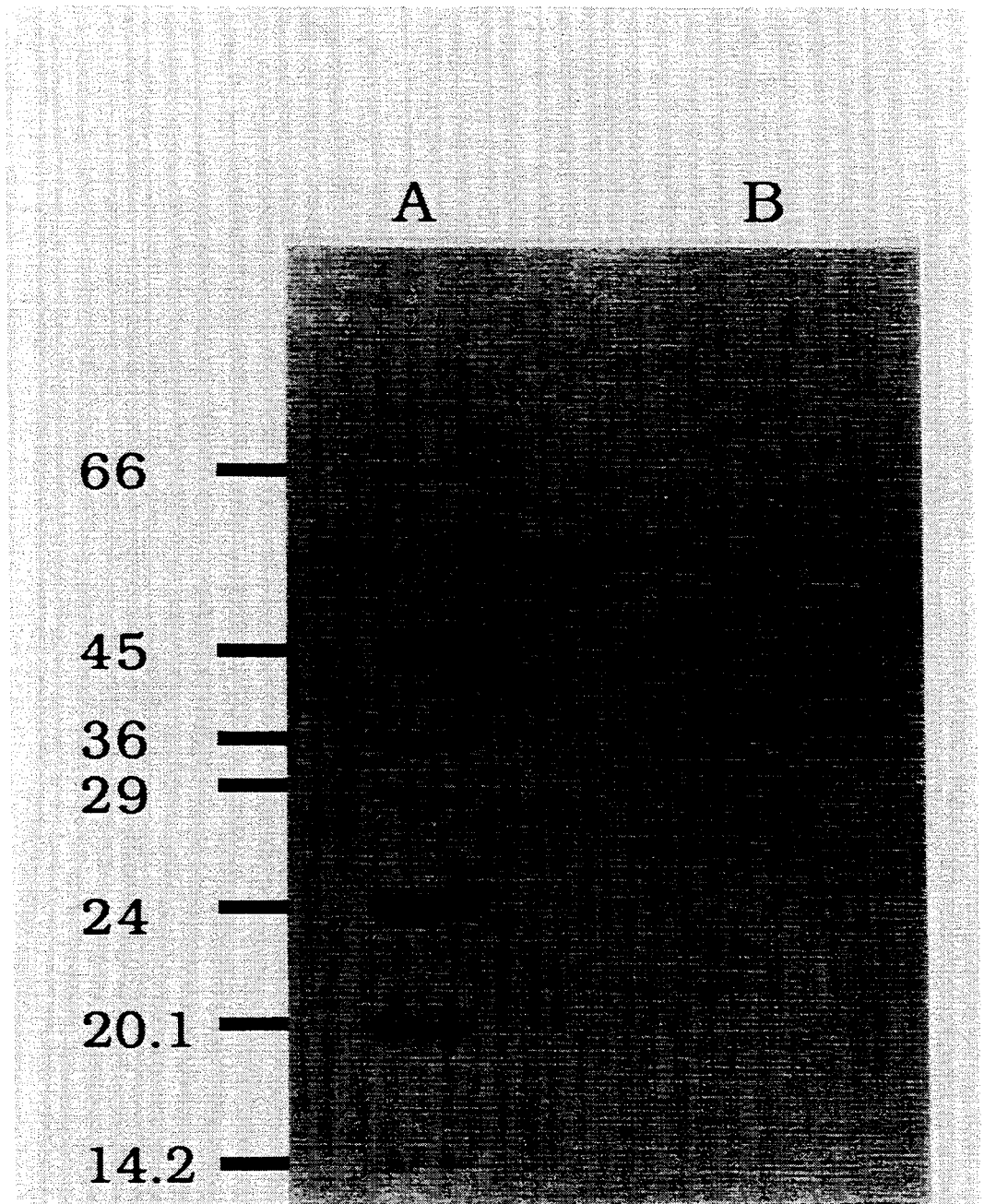
FIG. 1 is a photograph of the polyacrylamide electrophoresis gel described in Example 1, showing two columns of protein bands, as discussed more fully hereinafter. Column "A" shows the stained bands of proteins used as molecular weight standards, and column "B" shows the stained band of the novel phosphatase of the present invention.

Purification and Properties of a Specific 4-nitrophenylphosphatase Isolated from *Aspergillus niger*

The following example demonstrates how the novel phosphatase of the present invention was identified, and subsequently isolated from the filamentous fungal microorganism, *Aspergillus niger*. It also demonstrates how the unique phosphatase enzyme can be used in molecular cloning assays.

Organism and Media

*Aspergillus niger,* strain NRRL-3, was purchased from the American Type Culture Collection (ATCC, Rockville, Md.; cell culture No. 9029). It was grown in liter batches of liquid medium in 2-liter flasks. To determine whether the production of this novel phosphatase activity by *A. niger* would be affected by the type of culture medium in which the fungus was grown, the following different media were tested: Czapeck's medium (containing sucrose) (Komano T, Plant Cell Physiol. 16: 643–658, 1975); phosphate-limited Czapek's medium; glucose-Czapek's medium (an equal mass of glucose substituted for sucrose); and "corn steep liquor" medium. This latter medium contained, per liter of solution: 70 g glucose, 15.0 g calcium carbonate ($CaCO_3$), 1.12 g zinc sulfate ($ZnSO_4.7\ H_2O$), 0.6 g ammonium sulfate [$(NH_4)_2SO_4$], 0.26 g sodium phosphate ($NaH_2PO_4$), 5.0 ml "corn steep liquor," and distilled water to a final volume of one liter. The pH of the latter medium was adjusted to neutrality (pH 7.0) with 1M sodium hydroxide (NaOH). Flasks of the media were inoculated with spores from *A. niger* previously grown on enriched media (Markwell et al., Appl. Microbiol. Biotechnol. 30: 166–169, 1989) and incubated for five days at 25° C. on a rotary shaker at 125 revolutions per minute. The dense filamentous fungal structures called "mycelia" were separated from the culture supernatant fluid by filtration through plastic window screening, followed by washing with distilled water and squeezing to remove excess liquid. The mycelial mass was then processed for enzyme extraction as outlined below.

Enzyme Purification

The enzyme of the present invention is readily detected, as described above, by its specific hydrolytic dephosphorylation reactivity with the small synthetic substrate called 4-nitrophenylphosphate (4-NPP).

Fungal mycelia of *A. niger* grown in seven liters of corn steep liquor medium were harvested as outlined above. The mycelia (233 g wet weight) were then placed in a 1 liter square bottle with 500 ml of 10 mM Tris-hydrochloride (HCl) buffer (pH 8.0), 1 mM magnesium chloride (MgCl$_2$) at 4° C., and homogenized for 30 seconds with a Polytron homogenizer (2.0 cm diameter probe) set at its highest speed. After this mixture was centrifuged at 16,000 x g for 15 minutes, the supernatant, containing almost no phosphatase activity, was discarded. The pellet was resuspended in 400 ml of 10 mM Tris-HCl (pH 8.0), 1 mM MgCl$_2$, 2.5M sodium chloride (NaCl) at 4° C. and again homogenized for 30 seconds. The homogenate was then filtered through Whatman No. 1 filter paper with vacuum. The filtered crude enzyme solution was stored at 4° C. in light impermeable containers until used for final purification of the new DNA phosphatase.

In the initial step of purification of the DNA phosphatase, 200 ml of crude enzyme were mixed with 2 ml of 100 mM PMSF (dissolved in isopropanol), and 0.2 ml of 1M MgCl$_2$. This was gently shaken, and the centrifuged for 20 minutes at 17,000 RPM in a Sorval SS34 rotor. The pellet was discarded, and the clear supernatant fluid was collected and applied to a 12×2.5 cm column of Phenyl Sepharose CL-4B (Pharmacia) equilibrated in 10 mM Tris-HCl (pH 8.0), 1 mM MgCl$_2$, 2.5M NaCl. The column was then washed at a flow rate of 3 ml min$^{-1}$ with a step gradient consisting of the following: (i) 100 ml of 10 mM Tris-HCl (pH 8.0), 1 mM MgCl$_2$, 2.5M NaCl; (ii) 100 ml of 10 mM Tris-HCl (pH 8.0), 1 mM MgCl$_2$, 0.2M NaCl; and (iii) 100 ml of 10 mM Tris-HCl (pH 8.0), 1 mM MgCl$_2$. Fractions of ten ml were collected. The phosphatase activity, as determined in sensitive 4-NPP assays, came off the column as a peak with the last buffer solution and was pooled based on specific activity.

The pooled phosphatase activity eluted from the Phenyl Sepharose column was then applied to a 8×2.5 cm column of Q-Sepharose (Pharmacia) equilibrated with 10 mM Tris-HCl (pH 8.0), 1 mM MgCl$_2$. The column was washed until absorbance at 280 nm returned to zero as monitored with an Isco V$^4$ absorbance monitor. A 400 ml linear gradient of 0.0 to 0.4 M NaCl in 10 mM Tris-HCl (pH 8.0), 1 mM MgCl$_2$ was used to elute the phosphatase, at a flow rate of 1 ml per minute. Fractions of seven ml were collected, and the flow rate was 1 ml min$^{-1}$. The enzyme activity eluted from the column at approximately 0.15M NaCl; fraction numbers 38 to 44 were pooled based on specific phosphatase activity, as determined in 4-NPP assays.

The pooled fractions from the Q-Sepharose column were concentrated by pressure filtration through a YM-30 Diaflo membrane (Amicon). This concentrated sample was then applied to a 50×2.5 cm column of Superose-12 (Pharmacia) equilibrated with 10 mM Tris-HCl (pH 8.0), 1 mM MgCl$_2$, 0.1M NaCl. Fractions of 2 ml were collected at a flow rate of 0.2 ml per minute. Fraction numbers 30 to 36 were pooled and used for further experiments. Native molecular size calibration for the Superose-12 column utilized the following markers: lactate dehydrogenase (M$_r$ 135,000), bovine serum albumin (M$_r$ 66,000), carbonic anhydrase (M$_r$ 29,000) and horse heart cytochrome c (M$_r$ 12,400).

Electrophoresis

A 10% polyacrylamide gel containing the powerful, negatively charged detergent sodium dodecyl sulfate (SDS) was used to determine purity and molecular weight of the purified phosphatase. Molecular size standards used included the following: alpha-lactalbumin (14,200); soybean trypsin inhibitor (20,100); trypsinogen (24,000); bovine carbonic anhydrase (29,000); rabbit muscle glyceraldehyde-3-phosphate dehydrogenase (36,000); egg albumin (45,000); and bovine serum albumin (66,000). A 7% acrylamide native isoelectric focusing gel was used to determine the isoelectric point (referred to as "pI"). Standard proteins of known isoelectric point included the following: amyloglucosidase from *A. niger* (pI 3.6); glucose oxidase from *A. niger* (pI 4.2); soybean trypsin inhibitor (pI 4.6); bovine milk beta-lactoglobin A (pI 5.1); bovine carbonic anhydrase II (pI 5.4 and 5.9); and human carbonic anhydrase (pI 6.6). The cathode solution was 0.1M beta-alanine and the anode solution was 0.1M acetic acid.

Assays

*A. niger* phosphatase activity was routinely determined by monitoring, in a spectrophotometer set at an absorbance wavelength of 400 nm, the formation of p-nitrophenol generated by the hydrolysis of 4-NPP (purchased from Calbiochem). Non-enzymatic hydrolysis controls were routinely included. The phosphatase assay contained the following in a total volume of 1.0 ml: 8 mM 4-NPP; 25 mM Tris-HCl (pH 8.0); and 5 mM MgCl$_2$. The reaction, which was initiated by addition of the crude, mycelium-free supernatant fluid mentioned above, was carried out at 30° C. in a Varian DMS 70 spectrophotometer with a wavelength bandpass of 2 nanometers. Molar absorptivity of 4-nitrophenol at pH 8.0 was $1.62 \times 10^4$ M$^{-1}$ cm$^{-1}$.

Assays carried out at pH values other than pH 8.0 were done as end point determinations. For determination of pH optimum, buffer systems used were: 25 mM sodium acetate for pH 4.0 to pH 5.5; 25 mM 2-[bis(2-hydroxyethyl)amino]-2-(hydroxymethyl)-propane-1,3-diol for pH 6.0 to pH 6.5; and 25 mM Tris-HCl for pH 7.0 to pH 9.0. The reactions were terminated by adding 2.0 ml of 100 mM NaOH to the reaction mixtures. The amount of chromogenic 4-nitrophenol produced was determined from the absorbance at a wavelength of 400 nanometers using a molar absorptivity of $1.86 \times 10^4$ M$^{-1}$ cm$^{-1}$.

Determination of substrate specificity utilized the assay of inorganic phosphate (P$_i$) by reaction of phosphomolybdate with malachite green (Carter and Karl, J. Biochem. Biophys. Methods 7: 7-13, 1982) or the extraction of released $^{32}$P$_i$ into an organic phase (Shacter E Anal Biochem. 138: 416-420, 1984). Appropriate controls lacking enzyme sample were included. Assays were normally carried out in triplicate and included samples incubated with calf intestine alkaline phosphatase as positive controls. For all assays, one unit of activity was defined as the release of 1 umole phosphate per minute at 30° C. Specific activity was defined as units per milligram of protein. Protein concentration was determined by the bicinchoninic acid method of Smith et al. (Anal. Biochem. 150: 76–85, 1985).

Exonuclease and endonuclease activities of phosphatase preparations were investigated by incubation of 0.1 unit of *A. niger* phosphatase with either 1 microgram of supercoiled pUC8 (BRL) or 1.2 micrograms of Hind III digested phage-lambda DNA (Stratagene). Mobilities of the DNA samples on 0.8% agarose gel electrophoresis were compared to untreated samples. Incubations were carried out in 10 mM Tris-HCl (pH 8.0), 1 mM MgCl$_2$ at 37° C. for one hour.

Substrate Preparation

Histones (Histone III-S) and Phosphorylase-b enzyme were labeled with [gamma-$^{32}$P]ATP (ICN Radiochemicals) and the catalytic subunit of the bovine heart cAMP-dependent protein kinase. [Gamma-$^{32}$P]ATP was used as a substrate at a specific activity of 0.25 uCi per pmol.

Circular plasmid DNA (pUCS) was opened up and linearized with the use of the DNA-breaking enzyme Eco RI (Promega). The linear DNA molecule was then dephosphorylated with calf intestine alkaline phosphatase (Promega) and purified by phenol:chloroform:isoamyl alcohol (25:24:1) extraction and ethanol precipitation. The linearized DNA was then 5'-end labeled with [gamma-$^{32}$P]-ATP and polynucleotide kinase (Stratagene).

Unless otherwise noted, all materials were purchased from Sigma Chemical Co., St. Louis, Mo.

RESULTS

Effect of Medium on Phosphatase Production

The effect of different kinds of growth medium on the 4-NPP phosphatase activity of *A. niger* mycelia extracts was explored. Five days after inoculation, cultures were harvested and homogenized in a manner similar to that described for purification of the phosphatase. The extracts exhibited the following amounts of 4-NPP phosphatase activity per 10 g fresh mycelia: Czapek's medium (0.21 unit); phosphate-limiting Czapek's medium (0.06 unit); glucose-Czapek's medium (0.10 unit); and corn steep liquor medium (1.11 units). Corn steep liquor medium was found to promote the highest production levels of 4-NPP phosphatase activity. The yield of enzyme from cultures grown in other media was significantly less, with phosphate-limiting conditions producing the least amount of phosphatase activity. Based on the greater phosphatase activity from *A. niger* grown in corn steep liquor medium, this medium was adapted for use in all further studies.

Purification

Mycelia (approximately 233 g wet weight, average) were harvested from 7 liters of corn steep liquor medium, homogenized, and phosphatase was purified by sequential chromatographic fractionation on Phenyl Sepharose, Q-Sepharose and Superose-12. The purification procedure and enzyme enrichment at each step is summarized in TABLE 1.

TABLE 1

Purification scheme for *A. niger* phosphatase

| Purification Step | Total Activity (Units) | Total Protein (mg) | Specific Activity (Units/mg) | Recovery (%) | Fold Purification |
|---|---|---|---|---|---|
| Crude extract | 15.6 | 309 | 0.050 | 100 | — |
| Phenyl Sepharose | 6.88 | 8.28 | 0.832 | 44.1 | 17 |
| Q-Sepharose | 5.05 | 0.74 | 6.82 | 32.4 | 136 |
| YM30 concentration | 3.37 | 0.089 | 37.9 | 21.6 | 758 |
| Superose-12 | 2.02 | 0.023 | 87.8 | 12.9 | 1760 |

Size and Isoelectric Point

Analysis of the final fraction of purified *A. niger* phosphatase was done by polyacrylamide gel electrophoresis under denaturing condition in the presence of a detergent (see FIG. 1). As shown in FIG. 1, row B, electrophoresis under denaturing conditions revealed a single band of protein in the phosphatase preparation, equivalent to a size of 37,000 daltons. The sizes (x 10$^{-3}$) of marker proteins (as shown in row A) are indicated on the left hand (vertical) axis of the FIGURE. Approximately 2 micrograms of purified phosphatase (lane B) had been loaded onto the gel shown. The gel was stained with silver to reveal the protein bands.

In contrast to the above, elution of non-denatured enzyme from a Superose-12 column corresponded to a native molecular weight of approximately 80,000, indicating that the native protein was a dimer of two 37,000 dalton subunits.

In determining the native molecular charge of this protein, it is found in isoelectric focusing studies to have an isoelectric point (a "pI") of approximately 4.6. The isoelectric point (pI) was estimated from isoelectric focusing in polyacrylamide as 4.6.

pH Optimum

The pH optimum of the phosphatase for 4-NPP was determined using the end-point assay already described previously. Buffer systems employed were 25 mM sodium acetate for pH 4.0 to 5.5, 25 mM 2-[bis(2-hydroxyethyl)amino]-2-(hydroxymethyl)-propane-1,3-diol for pH 6.0 to 6.5, and 25 mM Tris-HCl for pH 7.0 to 9.0. The activity was evident over a broad pH range from pH 5 to 9 and displayed a maximum at pH 8.0.

Kinetics

The K$_m$ of the phosphatase for 4-NPP was determined as 0.77 mM from double reciprocal plots of enzyme velocity versus substrate concentration. The V$_{max}$ of the purified enzyme was 1.9 units per mg protein and the turnover number was 108 per second. The phosphatase showed a first-order inactivation with a half-life of 5.3 minutes when incubated in 10 mM Tris-HCl (pH 8.0) and 1 mM MgCl$_2$ at 50° C.

Substrate Specificity

In addition to 4-NPP, a variety of nucleotides, sugar phosphates, other organic phosphates and inorganic pyrophosphate (PP$_1$) were examined as potential substrates for the purified phosphatase using a spectrophotometric assay for inorganic phosphate (P$_i$) formation. Substrates were incubated with the enzyme for 15 minutes and the amount of P$_i$ liberated was measured and expressed relative to the hydrolysis of 4-NPP assayed with the same procedure (TABLE 2). For purposes of comparison, identical incubations were prepared in which an equivalent activity (using 4-NPP as substrate) of calf intestine alkaline phosphatase was included.

TABLE 2

Substrate specificity of *A. niger* 4-NPP and calf intestine phosphatases

| Substrate | Relative Activity *A. niger* | Calf Intestine |
|---|---|---|
| 8 mM 4-NPP | 100 | 100 |
| 1 mM 4-NPP | 58 | 103 |
| 2'-AMP | <1 | 134 |
| 3'-AMP | <1 | 83 |
| 5'-AMP | ≦1 | 102 |
| dAMP | <1 | 121 |
| ADP | <1 | 77 |
| ATP | ≦1 | 80 |
| DATP | <1 | 89 |
| 2'-GMP | <1 | 99 |
| 3'-GMP | <1 | 122 |
| 5'-GNP | ≦1 | 140 |
| UMP | <1 | 113 |
| Ppi | <1 | ND* |
| Glucose-6-Phosphate | <1 | 126 |
| Glucose-1-Phosphate | <1 | ND |
| 6-Phosphogluconic acid | ≦1 | ND |
| 4-Methylumbelliferyl Phosphate | <1 | 90 |

TABLE 2-continued

Substrate specificity of *A. niger* 4-NPP and
calf intestine phosphatases

| Substrate | Relative Activity | |
|---|---|---|
| | A. niger | Calf Intestine |
| alpha-napthylphosphate | ≦1 | 108 |

*ND, not determined

As shown in TABLE 2, significant dephosphorylation of any substrate other than 4-NPP by purified *A. niger* phosphatase could not be detected, whereas all substrates examined were hydrolyzed by the calf intestinal phosphatase. The *A. niger* phosphatase also failed to hydrolyze 4-nitrophenylacetate or bis-4-nitrophenylphosphate, indicating a lack of esterase and phosphodiesterase activity, respectively (data not shown). The amount of inorganic phosphate released from 4-NPP was stoichiometric with the formation of 4-nitrophenol, indicating that transphosphorylation reactions were not occurring to any significant extent.

To further examine one of these potential substrates at a greater level of sensitivity, the enzyme was incubated with [gamma-$^{32}$P]ATP under identical conditions and assayed for the liberation of $^{32}$P$_i$. No liberation above background was detected and hydrolysis of ATP appeared to occur at a rate less than one/ten-millionth of that observed with 4-NPP. Although ATP was able to inhibit the hydrolysis of 4-NPP, analysis revealed that the inhibition was competitive in nature, with a K$_i$ of 1.3 mM for ATP. Because the ATP concentration normally used in radioactive end-labeling reactions is near 1 uM (Maniatis T., Fritsch E. F., and Sambrook J.: *Molecular Cloning: A Laboratory Manual*, New York: Cold Spring Harbor Laboratory, 1982), the amount of inhibition of the phosphatase by ATP in a combined dephosphorylation/labeled-phosphorylation reaction would be negligible.

The purified *A. niger* phosphatase has a subunit size approximately equal to that of the catalytic subunits of many eukaryotic protein phosphatase enzymes, some of which hydrolyze 4-NPP, but when the purified phosphatase was incubated with either [$^{32}$P]histone or [$^{32}$P]-phosphorylase-a under the standard assay conditions the generation of $^{32}$P$_i$ from either phosphoprotein was not observed.

End-labeled linear pUC8 DNA (20 pmol 5'-ends) was incubated with 0.05 units of *A. niger* phosphatase (measured using 4-NPP as substrate) for 1 hour under standard assay conditions and 0.27 pmol $^{32}$P$_i$ was liberated. Calf intestine alkaline phosphatase was also incubated under identical conditions and 12.4 pmol $^{32}$P$_i$ was liberated. Controls lacking enzyme were incubated under identical conditions. Hydrolysis of DNA 5'-phosphate under these conditions occurred reproducibly at a rate of 10$^{-2}$% and 0.4% of that observed with 4-NPP with *A. niger* phosphatase, and calf intestine alkaline phosphatase, respectively. The activity observed probably represented actual phosphatase activity since the purified *A. niger* phosphatase contained no detectable endo- or exonuclease activity, and the assay, utilizing the formation of a phosphomolybdate complex and its extraction into toluene, was insensitive to nuclease activity.

Effect of Inhibitors and Divalent Cations

Prospective inhibitors were added to the standard assay with 4-NPP as substrate and inhibition was monitored and expressed as percent inhibition of the untreated sample (TABLE 3).

TABLE 3

| Effect of inhibitors on *A. niger* phosphatase activity | |
|---|---|
| Sample | Inhibition (%) |
| untreated | 0 |
| 1 mM EDTA | 8 |
| 10 mM EDTA | 94 |
| 1 mM orthophosphate | 11 |
| 1 mM orthophosphate | 26 |
| 10 mN orthophosphate | 39 |
| 1 mM PP$_i$ | 4 |
| 10 mM PP$_i$ | 56 |
| 1 mM sodium fluoride | 22 |
| 10 mM sodium fluoride | 80 |
| 1 mM iodoacetate | 96 |
| 1 mM N-ethylmaleimide | 75 |

The potent chelator of divalent cations, ethylenediamine-tetraacetate (EDTA), was found to be a strong inhibitor of the new phosphatase at 10 mM, suggesting a divalent metal requirement for catalytic activity. Orthophosphate and inorganic pyrophosphate produced a limited inhibition at the concentrations tested whereas sodium fluoride gave strong inhibition. Iodoacetate and N-ethylmaleimide, covalent modifiers of reactive sulfhydryls, were incubated with the phosphatase for 15 minutes at room temperature prior to assays. Treatments with both iodoacetate and N-ethylmaleimide strongly inhibited phosphatase activity, suggesting that modification of a sulfhydryl group may negatively affect enzymatic activity.

After treatment with EDTA, this chelator was removed from the enzyme by gel filtration and the specific activity of the 4-NPP phosphatase was measured following addition of various divalent cations (TABLE 4). Addition of 1 mM Mg$^{2+}$ provided a 20-fold stimulation of activity, but was only able to restore 39% of the specific activity measured prior to EDTA treatment. Added Mn$^{2+}$ produced a slight stimulation whereas Zn$^{2+}$ and Ca$^{2+}$ inhibited the enzymes activity even further.

TABLE 4

| Effect of divalent cations on *A. niger* phosphatase specific activity | |
|---|---|
| Sample | % of untreated |
| untreated | 100 |
| EDTA treated | 2 |
| 1 mM MgCl$_2$ | 39 |
| 5 mM MgCl$_2$ | 36 |
| 10 mM MgCl$_2$ | 36 |
| 0.1 mM MnCl$_2$ | 8 |
| 1 mM MnCl$_2$ | 8 |
| 0.01 mM ZnCl$_2$ | 2 |
| 0.1 mM ZnCl$_2$ | 1 |
| 1 mM ZnCl$_2$ | 0 |
| 0.1 mM CaCl$_2$ | 0 |
| 1 mM CaCl$_2$ | 0 |

End-labeling of Linear DNA Molecules

In the usual end-labeling process, the highly-reactive 5'-terminal phosphate group of the linear DNA molecule is first hydrolytically removed by the dephosphorylating enzyme, after which the activity of the phosphatase is destroyed by heat denaturation, with or without additional treatment with chemical denaturing agents, such as a detergent like SDS. The dephosphorylated DNA is then precipitated, washed, and reisolated free of the phosphatase enzyme and denaturing agents, in preparation for the next series of reaction steps of rephosphorylation, most commonly with a phosphate group bearing a detectable label. In a preferred embodiment, the labeled phosphate group is derived from the terminal high-energy phosphate group of a radiolabeled adenosine triphosphate (ATP) molecule. The labeled phosphate group is covalently linked at the 5'-terminal position of the treated DNA by the action of a polynucleotide kinase.

This dephosphorylation-rephosphorylation process, essential to most DNA end-labeling studies, is greatly simplified when the dephosphorylating enzyme will only react with one substrate, and can, therefore, remain in the reaction mixture without interfering in the subsequent steps of the reaction sequence. Because of its substrate specificity, such is the distinctiveness of the novel *A. niger* phosphatase enzyme of the present invention.

Therefore, the great distinction of this process, compared to other dephosphorylation/labeled-rephosphorylation procedures, is its simplicity: i.e., the *A. niger* phosphatase enzyme is not denatured or removed from the reaction mixture after it dephosphorylates the DNA molecule, as other phosphatase enzymes must be. Because it will not interact with the phosphate groups of the ATP, which are utilized in the next step of the reaction, the *A. niger* phosphatase is left in the reaction mixture, thereby eliminating at least one, if not two, time-consuming procedural steps in the entire end-labeling procedure.

While the present invention has been described in conjunction with preferred embodiments and specific examples, the description is not meant to limit it. One of ordinary skill, with the aid of the present disclosure, may be able to effect various changes, substitutions of equivalents and other alterations to the methods and compositions herein set forth. Therefore, the protection granted by Letters Patent should not be limited except by the language of the claims as set forth below.

What is claimed is:

1. A process for dephosphorylating a linear polylnucleotide substrate at the 5'-terminal position comprising contacting a phosphatase from *Aspergillus niger* with said linear polynucleotide substrate in an effective reaction medium at a pH of between about 7.0 to about 8.5 and at an effective temperature below the inactivation temperature of said phosphatase, said phosphatase having the following properties:
   a molecular weight of about 80,000 daltons,
   an isoelectric point of about pI 4.6,
   a half-life of about 5.3 minutes at about 50° C.,
   exhibits optimal enzymatic activity under neutral to slightly alkaline conditions of between about pH 7.0 to pH 8.5,
   removes the 5'-terminal phosphate group from a linear DNA polymeric molecule, and not the phosphate group from a monomeric adenosine triphosphate (ATP) molecule, and
   consists of two identical polypeptide subunits, said subunits having a molecular weight of about 37,000 daltons each.

2. The process of claim 1 wherein said polynucleotide substrate is RNA.

3. The process of claim 1 wherein said polynucleotide substrate is DNA.

4. The process of claim 3 wherein said DNA is single stranded.

5. The process of claim 3 wherein said DNA is double stranded.

* * * * *